United States Patent [19]
Koh et al.

[11] Patent Number: 5,989,990
[45] Date of Patent: Nov. 23, 1999

[54] TINOXIDE THIN FILM, PREPARATION THEREOF, AND GAS DETECTING SENSOR USING THEREOF

[75] Inventors: Seok Keun Koh; Hyung Jin Jung; Seok Kyun Song; Won Kook Choi, all of Seoul; Dongsoo Choi; Jin Seok Jeon, both of Ansan, all of Rep. of Korea

[73] Assignee: Korea Gas Corporation, Seoul, Rep. of Korea

[21] Appl. No.: 08/599,989

[22] Filed: Feb. 14, 1996

[30] Foreign Application Priority Data

Aug. 4, 1995 [KR] Rep. of Korea ............... 95-24120

[51] Int. Cl.$^6$ ............................................. C23C 14/32
[52] U.S. Cl. .................... 438/608; 438/609; 427/529; 427/561; 427/564
[58] Field of Search ........................ 438/608, 609, 438/679; 427/576, 529, 523, 531, 564, 561; 204/192.17, 192.29, 298.05

[56] References Cited

U.S. PATENT DOCUMENTS

| | | | |
|---|---|---|---|
| 4,091,138 | 5/1978 | Takagi et al. | 428/209 |
| 4,197,814 | 4/1980 | Takagi et al. | 118/726 |
| 4,740,267 | 4/1988 | Knauer et al. | 156/635 |
| 5,084,265 | 1/1992 | Harada et al. | 423/592 |
| 5,110,435 | 5/1992 | Haberland | 204/192.31 |
| 5,196,102 | 3/1993 | Kumar | 427/528 |
| 5,582,879 | 12/1996 | Fujimura et al. | 427/561 |
| 5,616,061 | 4/1997 | Potter | 445/24 |

OTHER PUBLICATIONS

Yamada, Isao and Gikan Takaoka, "Ionized Cluster beams: Physics and Technology", Jpn J. Appl. Phys., vol. 32 (1993) pp. 2121, May 1993.

H. Takaoka et al. *Crystallographic Properties of Tin Oxide Thin Films Prepared by R–ICB Technique*, pp. 143–146, Dept. of Electronics, Kyoto University.

*Primary Examiner*—Charles Bowers
*Assistant Examiner*—Matthew Whipple
*Attorney, Agent, or Firm*—Darby & Darby

[57] ABSTRACT

The present invention relates to tinoxide thin film, a process for manufacturing thereof comprising the step of depositing tin while providing oxygen or ionized oxygen around a substrate, and relates to a gas detecting sensor prepared by the use of such tinoxide thin film.

8 Claims, 5 Drawing Sheets

TINOXIDE THIN FILM, PREPARATION THEREOF, AND GAS DETECTING SENSOR USING THEREOF

BACKGROUND OF THE INVENTION

The present invention relates to tinoxide thin film, a prototype of an n-type semiconductor, of which optical band gap is about 3.5 eV, mainly used for transparent electrodes or for detecting reductive, inflammable gases ($H_2$, $CH_4$, $C_3H_8$, etc.). More specifically, the present invention relates to tinoxide thin film which satisfies nonstoichiometry/stoichiometry, respectively, the preparation thereof, and a gas-detecting sensor prepared by the use of such tinoxide thin film.

Conventional semiconductor-type gas detecting sensors are roughly divided into sintering type, thick film type and thin film type. Most inflammable gas sensors commercially available at present are bulk-type sensors prepared by a sintering process where powdery raw material is molded under pressure and then heat-treated at high temperature. However, bulk type sensors and thick film type sensors have lower sensitivity to gases compared to thin film type sensors, and are difficult to be mass-produced and require higher costs for production.

On the other hand, thin film type sensors are useful in that they can be easily prepared as microsensors, and have high sensitivity to gases.

Recently, research for developing microsensors using thin film material, particularly processes for preparing novel thin films in which rare elements can be easily doped have been extensively proceeded, because incorporation of rare elements in thin films is essential to increase the performance of sensors.

As thin films for manufacturing gas detecting sensors, tinoxide thin film is most widely used, and such tinoxide thin film should be homogeneous $SnO_2$ type so as to allow a dopant to exhibit the performances when the doping element is added to increase the electric and/or chemical characteristics of the tinoxide thin film.

For manufacturing the tinoxide thin film, processes for manufacturing ceramic thin films by the use of chemical vapor deposition(CVD) such as plasma enhanced (PE) CVD and metal organic (MO) CVD are known. However, it is almost impossible to control the thickness, orientation, crystallinity, density, and micropores of the thin films, using these known processes.

When physical vapor deposition process such as DC or RF sputtering, ion beam sputtering or ion assisted deposition (IAD) are used, it is possible to manufacture thin films varying organo metallic materials, bias potentials, compositions of the target etc. However, in these cases, it is difficult to control the thin film properties.

Takagi et al. prepared a $SnO_2$ thin film in a high vacuum chamber containing oxygen, using an ionized cluster beam deposition(ICBD) process [H. Takaoka, K. Matsubara and T. Takagi, Proc. 4th Symp. on Ion Sources and Ion Application Technol. Kyoto (1980), p143]. According to this process, however, the temperature of the substrate plate was as high as 400° C., and the obtained thin film was polycrystalline tin oxide thin film having large amount of Sn, SnO, $Sn_2O_3$ etc. admixed therein as well as $SnO_2$.

SUMMARY OF THE INVENTION

The present invention provides a process for manufacturing tinoxide thin film or the same doped with rare elements wherein tin is vapor deposited by an ion cluster beam deposition (ICBD) process with providing neutral oxygen gas or ionized oxygen gas around the sample to be deposited under a high vacuum region of $10^{-4}$ to $10^{-7}$ torr.

The present invention also provides tinoxide thin film having a thickness of not more than several thousand Å (angstroms), a surface roughness of not more than 10 Å, and a crystallinity of $SnO_2(200)$ and $SnO_2(110)$.

DETAILED DESCRIPTION OF THE INVENTION

Figure 1:
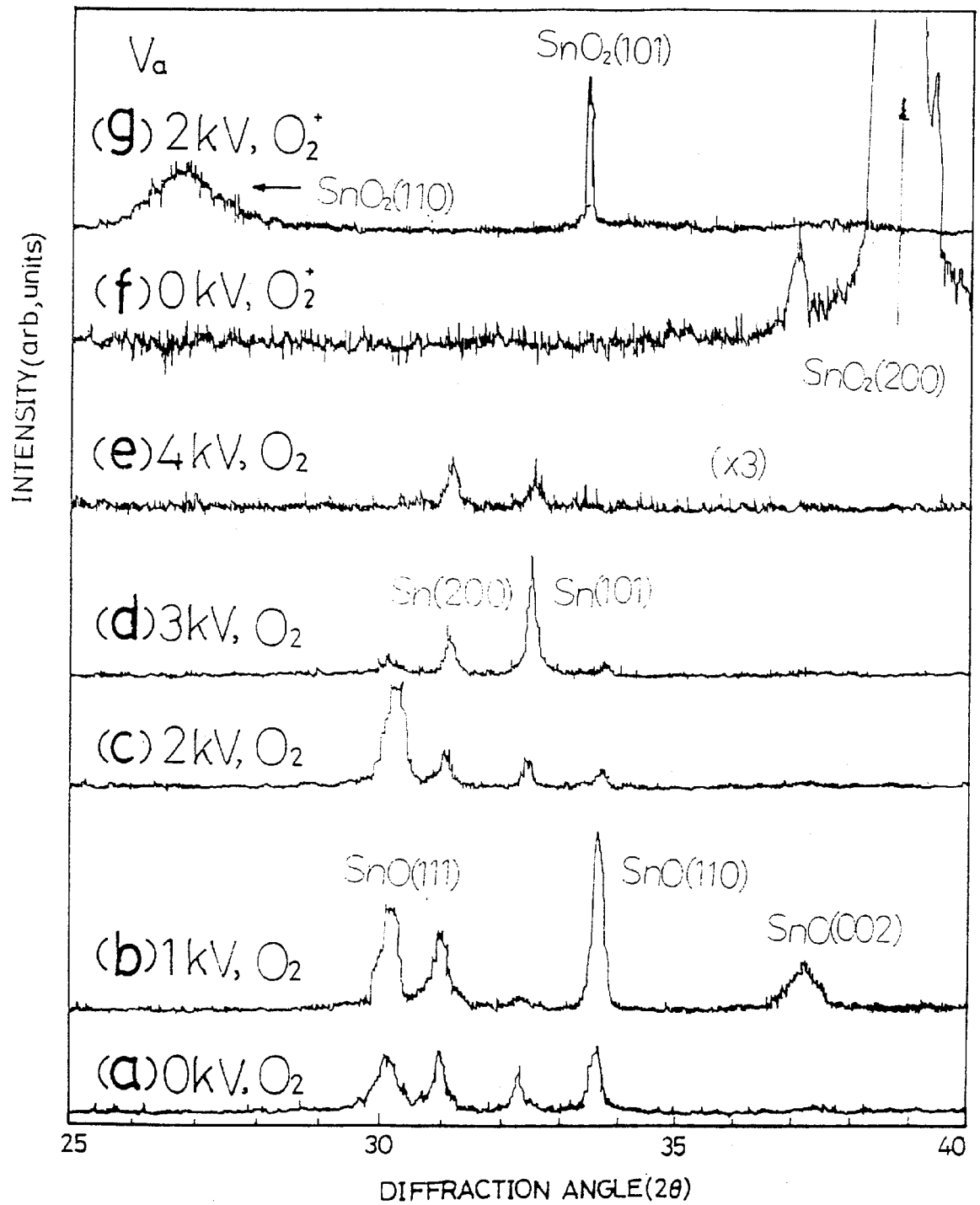
FIG. 1 is a graph showing an X-ray diffraction pattern where the deposition was performed while providing oxygen gas around the sample, and where the deposition was performed while providing ionized oxygen around the sample.
Figure 2:
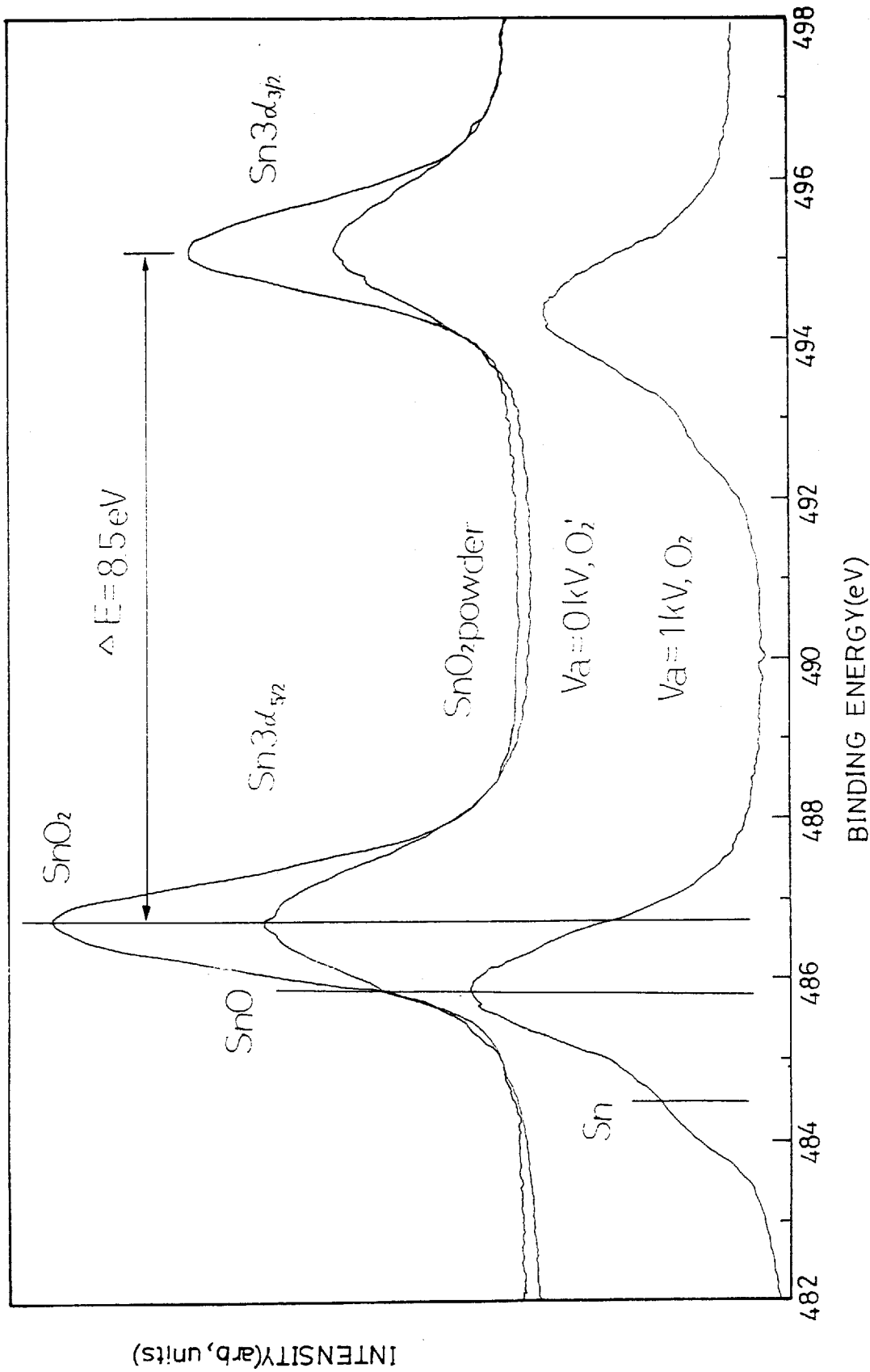
FIG. 2 is an X-ray photoelectron spectroscopy spectra of Sn binding energy of pure $SnO_2$ powder, $SnO_2$ (200) thin film deposited while providing ionized oxygen and thin film deposited while providing $O_2$.

The process of the present invention enables to provide $SnO_2$ thin film having a thickness of several thousand angstroms in a large scale at a lower cost, by controlling the energy of depositing particles to form a proper thin film at a lower substrate plate temperature with rapid nuclear formation to obtain a smooth surface of the thin film.

The thin films manufactured by the process according to the present invention have improved sensitivity and reproducibility. Also, the problem of power dissipation loss owing to the size can be solved by the present process.

The process according to the present invention for manufacturing $SnO_2$ thin film or $SnO_2$ thin film doped with rare elements, can be performed by a modification of a reactive ionized cluster beam deposition (ICBD) process or an ion assisted deposition (IAD) process.

The process for manufacturing tinoxide thin film according to the present invention is described as follows:

1) A substrate plate is installed, and Sn is placed in a crucible and deposition chamber and the pressure therein is maintained at not more than $10^{-6}$ torr;
2) Tin vapor particles or clusters are generated by raising the temperature of the crucible by applying a high potential of about 1,500 V between the crucible filament (CF) and the crucible itself, while operating the CF to emit thermoelectrons. The temperature of the crucible is set at 1350–1600° C. in order to maintain the vapor pressure of the vapor particles in the crucible at 0.1–1 torr;
3) The metallic tin generated as such is ionized by the use of ionization filament(IF) and ionization potential(IP);
4) The ionized tin is accelerated to the side of the substrate plate by applying 0–4 kV of acceleration potential to the substrate plate.

According to an embodiment of the present invention in which a reactive ionized cluster beam deposition process is applied, oxygen gas is provided around the sample when the vaporized tin metal is ionized and accelerated to the substrate plate in stage 4).

In the present invention, a conventional ionized cluster beam source for metal is utilized to generate tin particles or clusters for manufacturing tinoxide thin film.

In order to manufacture tinoxide thin film doped with a dopant, an additional dopant ICB source can be used.

The ion cluster beam source can control crystallinity and electronic and/or optical properties of the thin film by simply altering the ionization potential and acceleration potential of the ionized cluster.

As for the method providing oxygen gas around the sample, any suitable method may be applied. For example, oxygen gas can be provided by utilizing a ring-type muti-nozzle apparatus.

According to another embodiment of the present invention in which an ion assisted deposition process is applied, tinoxide thin film is manufactured by supplying ionized oxygen gas around the substrate plate when the vaporized tin metal is ionized and accelerated to the side of the substrate plate in stage 4).

In this case, oxygen may be ionized by a process such as plasma discharge. For example, oxygen may be ionized by the use of a gas ion gun. With use of a gas ion gun, the energy and current density of the ionized ions can be controlled.

FIG. 1 is an X-ray diffraction spectra of the thin film manufactured by altering the acceleration potential of the ionized Sn metal gas with the temperature of the substrate plate being ambient temperature, according to the present invention. It is recognized that the crystalline type can be changed by altering the acceleration potential. In case $O_2$ is used as an oxygen source, the crystallinity of the thin layer essentially comprised of SnO and Sn metal. Here, the SnO and Sn metal peak intensity ratios when the acceleration potential is 2 kV, almost equal the ideal peak intensity ratios in a bulk type structure, respectively. At an acceleration potential higher than 2 kV, SnO phase is hardly observed.

In case that ionized oxygen is utilized as the oxygen source, pure tinoxide thin film of single phase of $SnO_2(200)$ and $SnO_2(110)$ is obtained at acceleration potentials of 0 kV and 2 kV, respectively.

Figure 3:
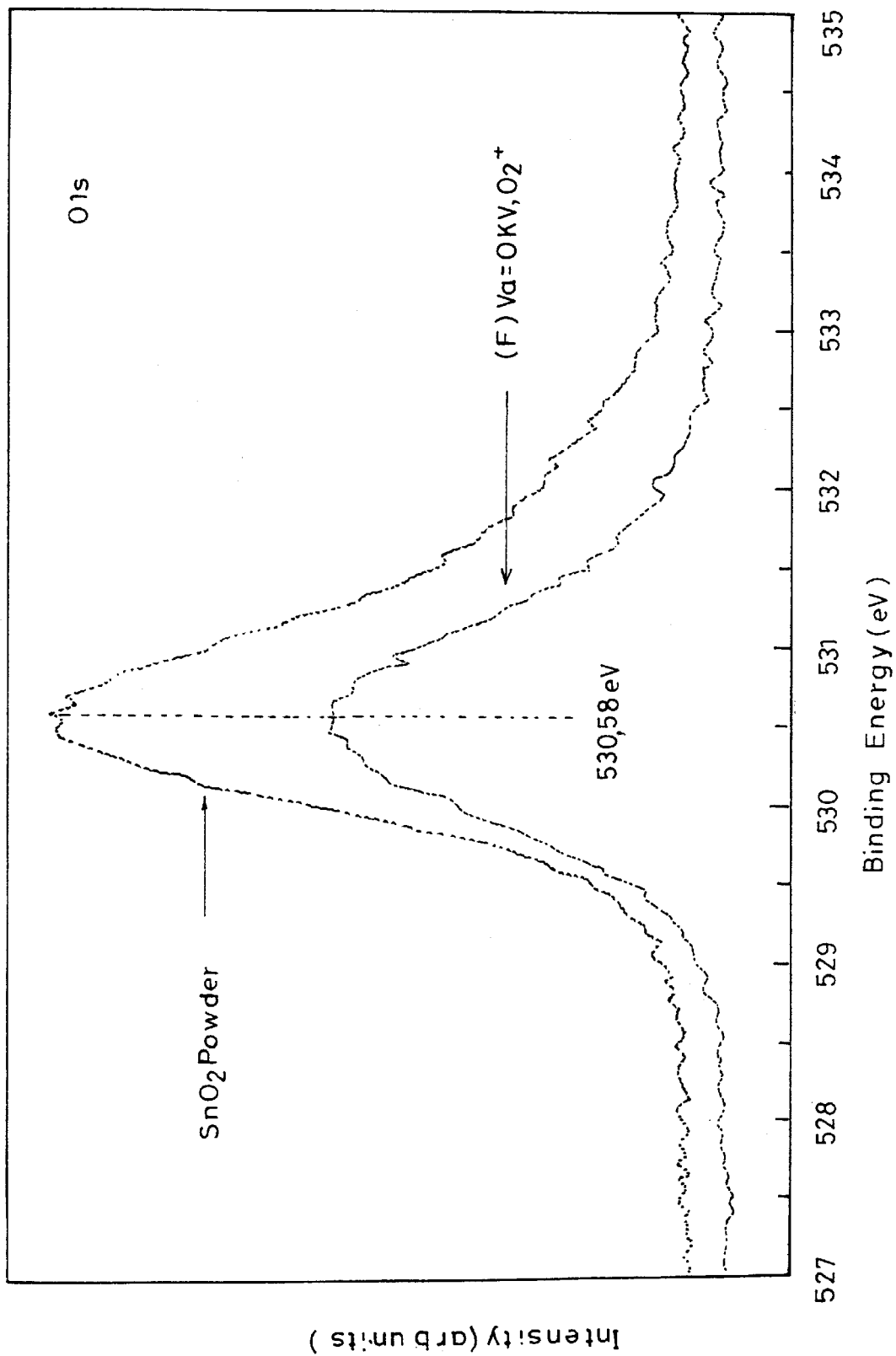
FIG. 3 shows X-ray photoelectron spectroscopy spectra of oxygen binding energy of pure $SnO_2$ powder and $SnO_2$ (200) thin film deposited while providing ionized oxygen.

As can be seen from in FIG. 3, $SnO_2(200)$ thin film obtained by the IAD process of the present invention is observed to have respectively determined at binding energies of 486.7 eV and 497.2 eV, which are completely equivalent to those values of $SnO_2$ standard powder. From these results, it can be recognized that the thin film prepared by the present invention contains $Sn^{4+}$ (stannous state).

Meanwhile, in case of the thin film prepared by using $O_2$ as the oxygen source according to the present invention, electron energies of Sn metal and SnO(stannic state: $Sn^{2+}$) are observed at the binding energies of 484.5 eV and 485.8 eV.

Figure 4:
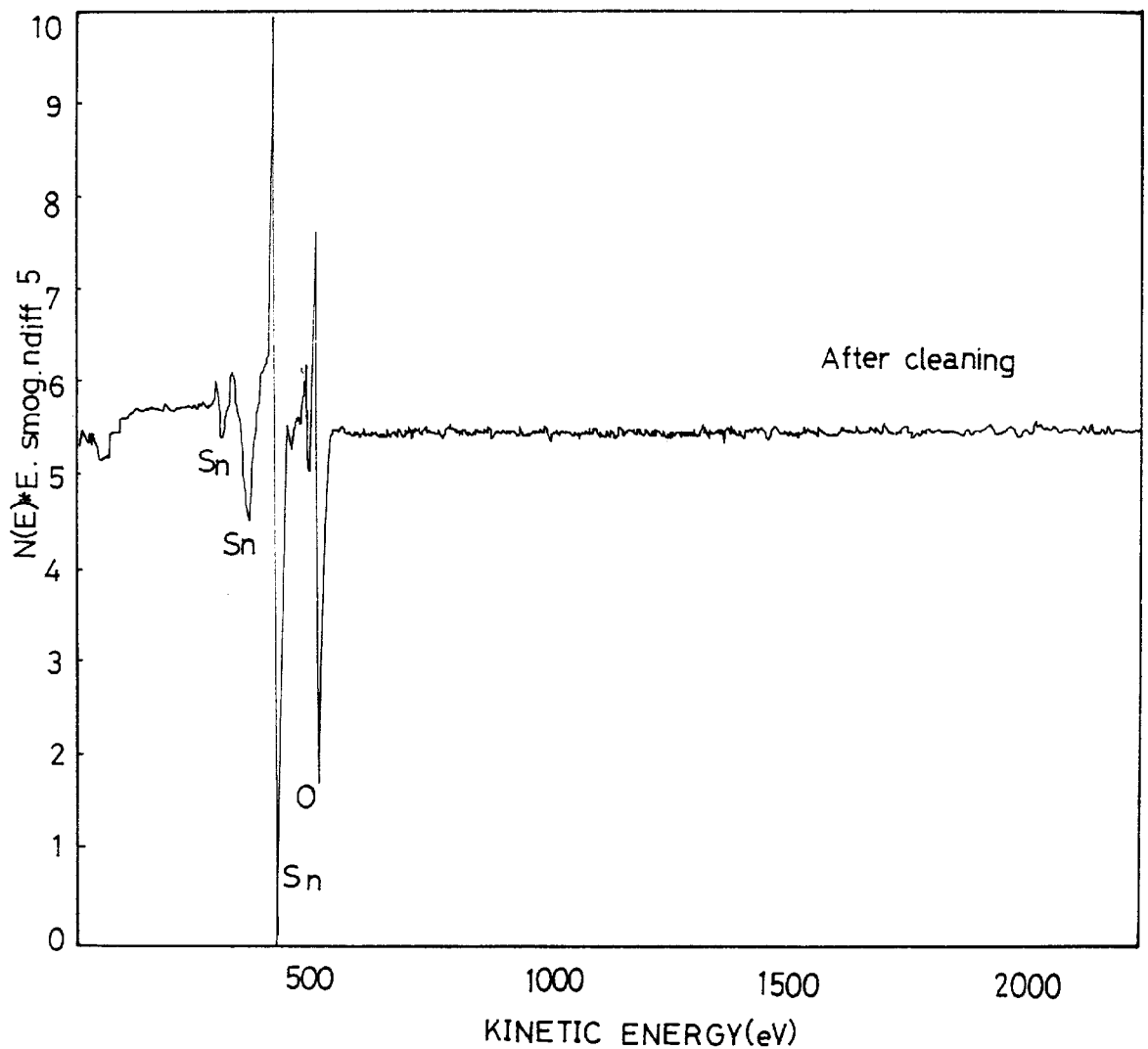
FIG. 4 is an Auger electron spectroscopy spectra of $SnO_2(200)$.

FIG. 4 shows the measured binding energies of oxygen in the thin film. Particularly, the oxygen binding energy of the $SnO_2(200)$ thin film manufactured by the IAD process of the present invention is 530.58 eV, which is equivalent to that for $SnO_2$ standard powder.

Figure 5:
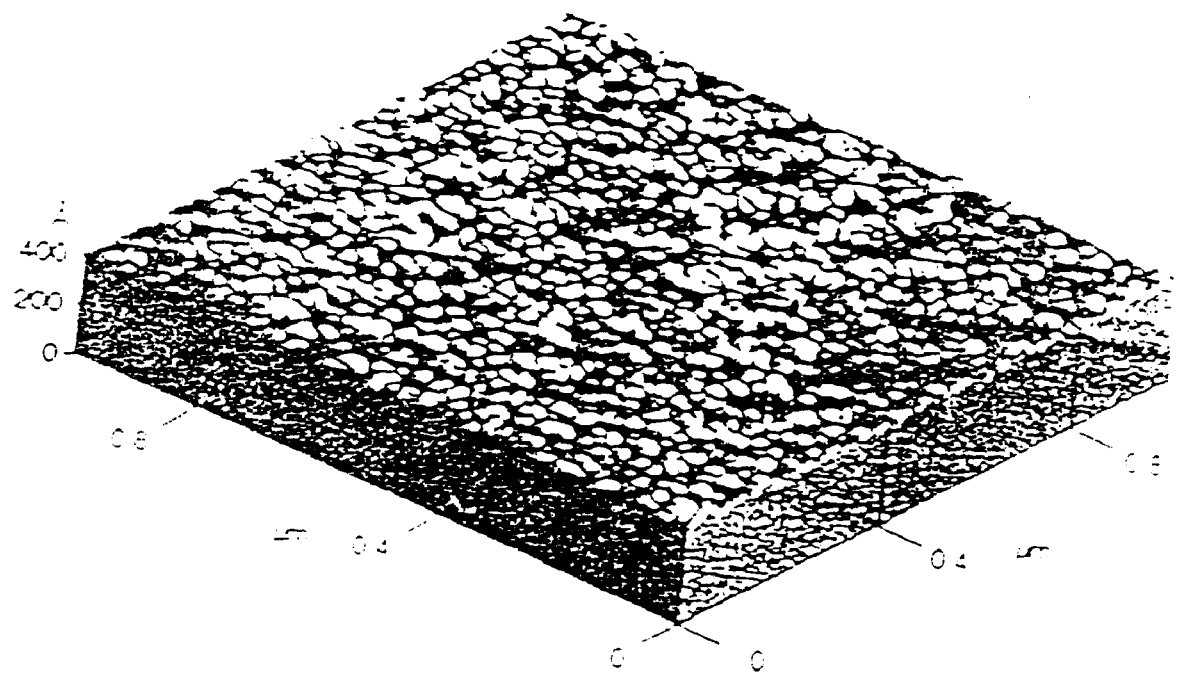
FIG. 5 is a photograph of the surface of $SnO_2(200)$ thin film(prepared by IAD process) observed by an atomic force microscope.

FIG. 5 shows the measurements of surface roughness of the $SnO_2(200)$ thin film manufactured by the IAD process, by observation through an atomic force microscope. It shows that the roughness is about 10 Å, which practically corresponds to the flatness of a silicon substrate, reflecting ion assisted effects during the deposition stage.

The peak to peak ratio of O/Sn in $SnO_2(200)$ prepared by the IAD process according to the present invention is 0.637.

While there has been illustrated and described what is at present considered to be the preferred embodiments of the present invention, it will be appreciated that numerous changes and modifications are likely to occur to those skilled in the art and it is intended in the appended claims to cover all those modifications and changes which fall within the true spirit and scope of the present invention.

What is claimed is:

1. A process for manufacturing a device having a tinoxide thin film on a silicon substrate plate comprising the steps of:

generating Sn as metallic vapor particles or clusters by ion cluster beam deposition (ICBD) process while providing oxygen around the silicon substrate plate on which the thin film is to be deposited;

ionizing the particles or clusters;

depositing the ionized Sn on the silicon substrate plate, under a high vacuum condition of not more than $10^{-6}$ torr; and wherein the silicon substrate plate is maintained at ambient temperature during the depositing step.

2. A process according to claim 1, further comprising providing an accelerating potential of not more than 4 kV on the silicon substrate plate.

3. A process according to claim 1, wherein the oxygen is provided as $O_2$.

4. A process according to claim 1, wherein the oxygen is provided as $O_2^+$.

5. A process according to claim 4, wherein the $O_2^+$ is provided by ionizing oxygen employing a gas ion gun.

6. A process according to claim 4, wherein the $O_2^+$ is provided with energy.

7. A process according to claim 4, wherein the deposited tinoxide thin film has a surface roughness of not more than 10 Å, and a crystallinity of $SnO_2(200)$ and $SnO_2(110)$.

8. A process as in claim 1 wherein the thin film is deposited having a thickness of not more than two thousand Å, a surface roughness of not more than 10 Å, and a crystallinity of $SnO_2(200)$ and $SnO_2(110)$.

* * * * *